United States Patent [19]

Vigouret

[11] 4,277,481

[45] Jul. 7, 1981

[54] ORGANIC COMPOUNDS

[75] Inventor: Jean-Marie Vigouret, Basel, Switzerland

[73] Assignee: Sandoz Ltd., Basel, Switzerland

[21] Appl. No.: 140,187

[22] Filed: Apr. 14, 1980

[30] Foreign Application Priority Data

Apr. 18, 1979 [GB] United Kingdom ............... 13456/79
Jan. 11, 1980 [GB] United Kingdom ............... 01020/80

[51] Int. Cl.$^3$ .................... A61K 31/48; A61K 31/475
[52] U.S. Cl. ...................................... 424/261; 424/262
[58] Field of Search ................................ 424/261, 262

[56] References Cited

U.S. PATENT DOCUMENTS 4,147,789  4/1979  Stütz et al. ........................... 424/261

OTHER PUBLICATIONS

B. Berde et al., "Ergot Alkaloids and Related Compound", (1978), pp. 534 & 539–543, Springer-Verlag Berlin Heidelberg New York.
Vigouret et al., "Pharmacology 16" (Suppl. 1) pp. 156–173, (1978).

*Primary Examiner*—Stanley J. Friedman
*Attorney, Agent, or Firm*—Gerald D. Sharkin; Robert S. Honor; Thomas O. McGovern

[57] ABSTRACT

6-methyl-8β-(2-pyridylthiomethyl)ergolene is useful in treating senile cerebral insufficiency and bladder incontinence.

11 Claims, No Drawings

ORGANIC COMPOUNDS

This invention relates to the compound, 6-methyl-8β-(2-pyridylthiomethyl)ergolene, also known by the code CF 25-397.

The preparation of this compound and pharmaceutical compositions containing this compound are known e.g. from U.K. Patent Specification No. 1,497,682. It has been indicated for use as a prolactin secretion inhibitor, an anti-parkinson agent and an anti-depressant on the basis of its pharmacological properties.

We have now found that the compound is surprisingly useful in completely new indications, namely in the treatment of senile cerebral insufficiency and in the treatment of bladder incontinence as indicated in single blind and double clinical trials.

The beneficial action of the compound in the treatment of cerebral sufficiency was observed in single and double blind trials effected e.g. as follows:

One trial covered 97 geriatric subjects suffering from mild to severe dementia as classified by standard methods, e.g. the Sandoz Clinical Assessment Geriatric scale (SCAG), which classifies the subject according to the following factors and sub-factors:

| Factor | Sub-factor |
| --- | --- |
| Cognitive Dysfunction | Confusion; Reduction of mental alertness; Impairment of recent memory; Disorientation; Impaired Self-care functions; Indifference to surroundings |
| Mood Depression | Anxiety; Mood depression, fatigue Emotional lability; lack of motivation or initiative |
| Agitation/Irritability | Irritability; Hospitaliy; Bothersomeness; Uncooperativeness |
| Somatic Symptoms | Anorexia; Dizziness |

The 97 subjects were divided into two groups: 50 subjects on the compound and 47 subjects on placebo only. The trial medication was presented in separate one week blister packs containing 2.5 mg tablets of the compound or placebo tablets of identical appearance, according to the following daily schedule:
1st week: 1 compound tablet +1 placebo tablet (Total daily dose=2.5 mg) or 2 placebo tablets.
2nd week: 2 compound tablets (Total daily dose 5 mg) or 2 placebo tablets.
3rd week: 3 compound tablets (Total daily dose 7.5 mg) or 3 placebo tablets.
4th–9th week: 4 compound (Total daily dose 10 mg) or 4 placebo tablets.

Each subject was rated at the end of the 1st, 2nd, 3rd, 6th and 9th week by a physician according to the SCAG scale. By the 3rd week the beneficial action of the compound was observed. In the 6th week, there was already a significant qualitative improvement and in the 9th week there was a statistical improvement in the four SCAG factors.

It was observed that the improvement was greater with subjects suffering from mild or moderate dementia than those suffering from severe dementia.

As indicated by the above clinical trials, the compound is useful for the treatment of senile cerebral insufficiency, e.g. for increasing vigilance in geriatric subjects.

The present invention accordingly provides in one aspect a method for treating senile cerebral insufficiency which comprises administering a therapeutically effective amount of the compound 6-methyl-8β-(2-pyridylthiomethyl)-ergolene to a subject in need of such treatment. For this use, the exact amount of compound to be administered will naturally depend on the subject to be treated, the severity of conditions, the mode of administration etc. From the above trials and tolerability trials a satisfactory daily dose is from about 1 to about 20 mg of the compound. For oral administration a satisfactory daily dose is from about 2.5 to about 15 mg, e.g. 2.5 to 5 mg, 2.5 to 10 mg or 2.5 to 12 mg. On average the preferred daily dose is about 7.5 mg.

The daily dose may be administered as a single dose, e.g. in sustained release form, or in divided doses 2 to 4 times a day containing about 0.25 to about 10 mg of the compound. For oral administration a satisfactory unit dosage form contains from about 1 to about 2.5 mg of the compound.

The beneficial action of the compound in the treatment of bladder incontinence was observed in single and double blind clinical trials.

One single blind clinical trial covered 9 women and 1 man (age 79–93) suffering from nocturnal, periodic or permanent bladder incontinence, of whom two subjects sufferred so badly that they required the permanent use of urine collectors. 7.5 mg of the compound was administered p.o. in divided doses three times a day for 12 weeks. Within a week a significant improvement was noted in 4 subjects, and after two weeks the subjects having urine collectors had improved so much that they did not need to use them.

A double blind clinical trial covered 16 subjects (8 subjects on the compound and 8 subjects on placebo). Administration of 2.5 mg p.o. thrice daily of the compound over 12 weeks led to a clinically relevant significant improvement in 6 subjects in the compound group, compared with 1 subject in the placebo group.

As indicated by the above trials, the compound is useful in the treatment of bladder incontinence, e.g. periodic, permanent, stress-induced, nocturnal, bladder incontinence, in subjects of all ages.

The present invention accordingly provides in another aspect a method for the treatment of bladder incontinence which comprises administering a therapeutically effective amount of the compound 6-methyl-8β-(2-pyridylthiomethyl) ergolene to a subject in need of such treatment.

For this use, the exact amount of compound to be administered will naturally depend on the subject to be treated, the severity of the conditions, the mode of administration etc. In general a daily dose of from about 1 to about 20 mg, is satisfactory. For oral administration a daily dose of from about 5 to about 20 mg e.g. 7.5 mg is suitable.

The daily dose may be administered as a single dose, e.g. in sustained release form, or in devided doses 2 to 4 times a day containing e.g. from about 1 to 6 mg of the compound.

The compound may be administered in free base form or in pharmaceutically acceptable acid addition salt form, conveniently the hydrogen tartrate form.

The compound may be administered on its own or in the form of pharmaceutical compositions. The present invention accordingly provides in a further aspect a pharmaceutical composition for treating senile cerebral insufficiency or bladder incontinence comprising as active agent the compound 6-methyl-8β-(2-pyridylthiomethyl) ergolene.

The known pharmaceutical compositions are suitable and may be made by conventional techniques to be in the form of capsules, tablets, suppositories, dispersible powders, syrups, elixirs, suspensions or solutions as appropriate for enteral or parenteral administration. Preferably unit dosage forms are used. The compositions may contain conventional pharmaceutical excipients, e.g. diluents and carriers, such as water, alcohols, natural or hardened oil and waxes, calcium and sodium carbonate, calcium phosphate, kaolin, talc and lactose. Other excipients which may be used include suspending agents, lubricating agents, disintegrating agents, etc.

Compositions in tablet form may be coated by conventional techniques to delay disintegration of the tablet and/or absorption of the active ingredient in the gastro-intestinal tract and thereby provide sustained action over a long period.

In a further aspect the present invention provides a pack or dispenser device containing the compound 6-methyl-8β-(2-pyridylthiomethyl) ergolene for use in the treatment of senile cerebral insufficiency, or in the treatment of bladder incontinence. The pack or dispenser device may contain for example a plurality of unit dosage forms containing the substance. These may be packed in metal or plastic foil, e.g. as in a blister pack. The pack or dispenser device may be together with instructions for administration of the compound, e.g. one unit dosage form of the compound at a specific time or specific times of day, e.g. at meal times or before retiring to sleep.

Examples of compositions that can be used are as follows:

| Capsule | |
|---|---|
| Component | Weight (mg) |
| 6-methyl-8β-(2-pyridylthiomethyl)ergolene hydrogen tartrate | 3.04 ((= 2.5 mg base) |
| Corn Starch | 60 |
| Lactose (200 mesh) | 232.46 |
| Silica (Colloidal) | 1.5 |
| Magnesium stearate | 30 |
| Total | 300 mg |

Sufficient amounts of the above components are mixed in conventional manner and filled into gelatine capsules.

| Tablet | |
|---|---|
| Component | Weight (mg) |
| 6-methyl-8β-(2-pyridylthiomethyl)ergolene hydrogen tartrate | 3.04 (2.5 mg base) |
| Lactose | 177.46 |
| Microcrystalline cellulose | 46 |
| Silica (Colloidal) | 1.2 |
| Magnesium stearate | 2.3 |
| Total | 230 mg |

Sufficient amount of the above components are mixed in conventional manner granulated and pressed to form tablets.

Sterile suspension for injection and oral liquid suspension

The following pharmaceutical compositions are formulated with the indicated amount of active agent using conventional techniques. The injectable suspension and the oral liquid suspension represent formulations useful as unit doses. The injectable suspension is suitable for administration once a day whereas the oral liquid suspension is suitably administered 3 times per day.

| Ingredient | Weight Sterile injectable suspension | Weight Oral liquid suspension |
|---|---|---|
| 6-methyl-8β-(2-pyridylthiomethyl)ergolene hydrogen tartrate | 5 mg | 2.5 mg |
| Sodium carboxy methyl cellulose | 1.25 mg | 12.5 mg |
| Methyl cellulose | 0.4 mg | — |
| Polyvinylpyrrolidone | 5 mg | — |
| Lecithin | 3 mg | — |
| Benzyl alcohol | 0.01 mg | — |
| Magnesium aluminum silicate | — | 47.5 mg |
| Flavour | — | q.s. |
| Color | — | q.s. |
| Methyl paraben, USP | — | 4.5 mg |
| Propyl paraben, USP | — | 1.0 mg |
| Polysorbate 80(e.g. Tween 80, USP) | — | 5 mg |
| Sorbitol solution, 70% USP | — | 5 mg |
| Buffer agent to adjust pH for desired stability | q.s. | q.s. |
| Water | (1) | (2) |

(1) for injection, q.s. to 1 ml.
(2) q.s. to 5 ml.

What we claim is:

1. A method of treating senile cerebral insufficiency, or treating bladder incontinence which comprises administering a therapeutically effective amount of the compound 6-methyl-8β-(2-pyridylthiomethyl)ergolene to a subject in need of such treatment.

2. A method according to claim 1 wherein the subject is suffering from mild to moderate dementia.

3. A method according to claim 1 wherein from 1 to 20 mg of the compound is administered daily.

4. A method according to claim 1 wherein from 2.5 to 5 mg of the compound is administered daily.

5. A method according to claim 1 wherein the subject is suffering from senile cerebral insufficiency.

6. A method according to claim 5 wherein the compound is administered in unit dosage form containing from 0.25 to 10 mg of active agent.

7. A method according to claim 5 wherein the compound is administered in unit dosage form containing 2.5 mg of active agent.

8. A method according to claim 1 wherein the subject is suffering from bladder incontinence.

9. A method according to claim 8 wherein from 5 to 20 mg of the compound is administered daily.

10. A method according to claim 8 wherein the compound is administered in unit dosage form containing from 1 to 6 mg of the compound.

11. A method according to claim 10 wherein the compound is administered in unit dosage form containing 2.5 mg of the compound.

* * * * *